United States Patent [19]

Herrera

[11] Patent Number: 5,529,489
[45] Date of Patent: Jun. 25, 1996

[54] LOCKING ORTHODONTIC BAND GAUGE

[75] Inventor: Joan Herrera, Trujillo Alto, Puerto Rico

[73] Assignee: Commonwealth of Puerto Rico, San Juan, Puerto Rico

[21] Appl. No.: 248,681

[22] Filed: May 25, 1994

[51] Int. Cl.⁶ .................................................... A61C 3/00
[52] U.S. Cl. ................. 433/3; 33/514; 33/555.4
[58] Field of Search ................... 433/3, 23, 72; 33/513, 514, 555.1, 555.4, 484, 485, 486

[56] References Cited

U.S. PATENT DOCUMENTS

| | | |
|---|---|---|
| 181,671 | 8/1876 | Greensfelder . |
| 596,022 | 12/1897 | Aber .......................... 33/514 |
| 780,919 | 1/1905 | Shockley .................... 33/514 |
| 1,448,222 | 3/1923 | Johnston et al. . |
| 1,653,016 | 12/1927 | Mellor ........................ 33/485 |
| 1,887,220 | 11/1932 | Stuckeman ................. 33/486 |
| 2,231,121 | 2/1941 | Hormann .................... 33/514 |
| 5,212,871 | 5/1993 | Luccarelli .................. 33/555.4 |
| 5,269,069 | 12/1993 | Min ............................ 33/555.4 |

Primary Examiner—Robert P. Swiatek
Assistant Examiner—Elizabeth Shaw
Attorney, Agent, or Firm—Oblon, Spivak, McClelland, Maier & Neustadt

[57] ABSTRACT

A locking orthodontic band gauge for determining an orthodontic band size. An elongated main portion is provided with a locking indicator assembly slidably mounted thereon. A loop cooperates with the main portion and indicator assembly such that when the indicator assembly is slid along the main portion, the size of the loop circumference changes. A series of locking portions are provided and spaced along the length of the elongated main portion at discrete positions and cooperate with the locking indicator assembly to selectively lock the indicator assembly at the discrete positions. Alternatively the orthodontic band gauge includes a probe for supporting a gauge tape such that the gauge tape can be fitted around the tooth when the probe is inserted into a patient's mouth. The probe has an indicator associated therewith and moveable relative to the probe for indicating the orthodontic band size of a patient's tooth when the gauge tape is fitted around the tooth. A locking mechanism is provided that positively locks the indicator relative to the probe such that the indicator is maintained stationary during an orthodontic band size fitting.

20 Claims, 9 Drawing Sheets

LOCKING ORTHODONTIC BAND GAUGE

BACKGROUND OF THE INVENTION

1. Field of the Invention

The field of the invention relates to orthodontistry, and, more particularly, to an orthodontic prefabricated band gauge for determining the correct orthodontic band size for a tooth.

2. Description of the Related Art

The orthodontic treatment of the posterior part of the orthodontic cavity is similar to the treatment for molar and pre-molar teeth. The use of pre-fabricated orthodontic bands cannot be prescinded or put aside because these teeth are the basis of movement performed over other teeth. Because these teeth differ in measurement and shape, a measurer of pre-fabricated orthodontic bands must determine the exact measurement of the tooth in order to choose the exact band needed for the tooth in orthodontic treatment.

An orthodontic pre-fabricated band is a ring shaped band usually made of metal. The orthodontist places the orthodontic pre-fabricated band around the tooth and selects the bands to be used. The selected pre-fabricated orthodontic band is then cemented. The band is then crimped tightly about the tooth and the cement is let dry, completing the procedure.

It is critical that the size of the band chosen by the orthodontist is correct because the band is permanently cemented to the tooth. Moreover, orthodontic bands come in different shapes to accommodate different types of teeth, such as bicuspids, and molars. Since the teeth vary in size and shape, an orthodontist cannot rely on judgment alone, but must measure the circumference of the particular tooth fitted for an orthodontic band with an orthodontic instrument.

A circular micrometer is commonly used as an orthodontic instrument to measure the millimeter circumference of a tooth in order to aid an orthodontist in selecting the size of an orthodontic band. Generally, a circular micrometer is a device used to measure any cylindrical object, the micrometer having one end of a flexible tape measure fixed to an elongated bar and the other end slidably mounted along the bar such that a loop is formed at an end of the micrometer. The loop is placed around an object and the tape is slidably adjusted along the bar to tighten the loop about the object. The micrometer includes a scale so that an operator may read the circumference measurement of the object. In orthodontic practice, the circumference of a tooth is measured and an orthodontic pre-fabricated band size is selected to be fitted on the tooth.

Orthodontists have found that the circular micrometer is inadequate for prefabricated orthodontic band measurement because this device was not devised specifically for orthodontic practice. Different orthodontic bands must actually be placed on the tooth to determine the correct band size even when using a circular micrometer. More importantly, improper selection of the orthodontic band size has often caused patients to return to the orthodontist's office to have cemented orthodontic bands replaced. What is required is an orthodontic instrument that indicates the correct size of a prefabricated orthodontic band for a tooth more accurately, so that the number of orthodontic bands attempted for fitting on a tooth is reduced.

Oral infections, a patient's comfort and cost are three basic factors that need be considered when devising any new orthodontic instrument for more accurately measuring the correct orthodontic pre-fabricated band size of a tooth. Such an orthodontic instrument will satisfy these three factors by performing more efficiently.

First, orthodontic instruments should be designed to reduce the possibility of oral infection. The instrument should be easily sterilized, and also should increase the efficiency of orthodontic procedures so that less time is required working within a patient's mouth, therefore creating less of a chance for an oral infection to occur. An orthodontic instrument must especially aid in preventing oral infections because this device is in direct contact with the traumatized orthodontic tissue. Repeated placement of orthodontic bands during a fitting on a patient's tooth will cause the gums to be irritated, further increasing the risk of infection. In the case where a cemented orthodontic band needs to be replaced, greater trauma is caused to the orthodontic tissue and the risk of infection is again increased.

Second, an orthodontic instrument for more accurately determining an orthodontic band size should be designed to be comfortable to a patient.

Third, an orthodontic instrument for more accurately determining an orthodontic band size should reduce the cost of the orthodontic procedure. Each orthodontic band that is fitted on a tooth and is found to be the incorrect size must be thrown away at cost for purposes of sanitation.

In summary, an orthodontic band gauge with an indicator is needed to indicate the correct size of prefabricated orthodontic bands for a particular tooth thereby decreasing the likelihood of oral infection, discomfort to the patient and cost. Specifically, such a gauge should lock the indicator in place so that a correct reading of the orthodontic band size is achieved despite removing the gauge or shifting of the patient. Further, the gauge must allow an operator to tighten the gauge loop firmly about the tooth to achieve a correct reading because the loop material may be substantially rigid to fit between tightly spaced teeth. In addition, the indicator should be easily read.

The prior art does not fulfill the need for an orthodontic band gauge that determines the correct prefabricated orthodontic band size because the prior art offers a mere circular micrometer. For example, U.S. Pat. No. 2,231,121 issued to Hörmann discloses a band-type micrometer that does not consider the above objectives. This device consists of the common features of a circular micrometer, having a loop for measuring the circumference of teeth and a slidable member that adjusts the size of the loop. As discussed, a circular micrometer similar to the disclosed Hörmann device is inadequate as an orthodontic instrument for more accurately determining an orthodontic band size. Hörmann nowhere teaches the use of this micrometer for determining correct orthodontic band sizes. Further, this device utilizes mere friction forces to lock the slidable member in place. As discussed, an orthodontic band gauge must be able to indicate the correct orthodontic band size even when fitted between tightly spaced teeth, removed from the teeth or jostled by the patient. The arrangement disclosed by Hörmann is inadequate to indicate an orthodontic band size accurately under these conditions because the friction force is not sufficient to lock the slidable member in place for a correct measurement.

Further, Hörmann does not disclose any device that pulls the loop sufficiently tight about the tooth. The slidable member is operated manually and is inadequate to tighten the device, especially when an orthodontist must operate from within the patient's mouth. A particular problem with the Hörmann device is that it discloses a loop that has one end attached to the device. If the loop is pinched between teeth, the loop will be unable to tighten past the pinching point because the loop only tightens from one side.

In addition, Hörmann does not disclose any means by which the device is easily read. An orthodontist must read the measurement while the Hörmann device is within the mouth, attached to a tooth. This increases the likelihood of an incorrect orthodontic band fitting because the device is difficult to read inside a mouth or might be thrown off due to the orthodontist's relocating the device in order to read the measurement.

In conclusion, the Hörmann device does not fulfill the requirements of an orthodontic band gauge and, therefore, would not adequately measure the correct band size for a particular tooth. As a result, this device would not be adequately sanitary, painless and inexpensive.

SUMMARY OF THE INVENTION

A locking orthodontic band gauge for determining an orthodontic band size is provided that fulfills the above requirements and adequately measures the correct band size for a particular tooth. In one embodiment, an elongated main portion is provided with a locking indicator assembly slidably mounted thereon. A loop cooperates with the main portion and indicator assembly such that when the indicator assembly is slid along the main portion, the size of the loop circumference changes. A series of locking portions are provided and spaced along the length of the elongated main portion at discrete positions and cooperating with said locking indicator assembly to selectively lock the indicator assembly at the discrete positions. In another embodiment, the locking orthodontic band gauge includes probe means for supporting a gauge tape such that the gauge tape can be fitted around a tooth by insertion of the probe means into a patient's mouth. Indicating means are associated with the probe means and movable relative therewith for indicating the orthodontic band size of a patient's tooth when the gauge tape is fitted around the tooth. Locking means positively lock the indicating means relative to said probe means such that the indicating means is maintained stationary during an orthodontic band fitting.

Accordingly, one object of the present invention is to provide a novel and more accurate orthodontic band gauge so that the selection of the prefabricated orthodontic band is made more efficient, thereby reducing the likelihood of oral infection, discomfort to the patient and cost;

Another object of the present invention is to provide an orthodontic band gauge that accurately measures an orthodontic band size;

Another object of the present invention is to provide an orthodontic band gauge that fits between tightly spaced teeth;

Another object of the present invention is to provide an orthodontic band gauge that allows an operator to fasten the band gauge loop tightly about a tooth;

Another object of the present invention is to provide an orthodontic band gauge with an indicator that is easily read; and Another object of the present invention is to provide an orthodontic band gauge that locks the band gauge tape into place.

In summary, a locking orthodontic band gauge is provided that satisfies the above objects, particularly, the locking element allows an orthodontist to perform an orthodontic band fitting more efficiently and thereby reduce the likelihood of oral infection, discomfort to the patient and cost. This same locking element allows accurate measurement of an orthodontic band size because this element positively locks the indicator assembly inplace, thereby avoiding misreading from movement of the orthodontic band gauge. This locking element also allows an operator to remove the locking orthodontic band gauge from tightly spaced teeth with no space out disturbing the orthodontic band size indicated. The elongated main portion or probe means cooperates with the indicator assembly such that an operator is able to assert leverage on the locking indicating assembly, thereby fastening the gauge loop tightly about a tooth. The elongated main portion and probe means are sufficiently long to be inserted deep into a patient's mouth, allowing the indicator to be easily read. Therefore, the locking element enables an operator of the locking orthodontic band gauge to lock the band gauge tape in place, thereby satisfying the above objectives.

Other objects, features, and advantages of the present invention will become apparent from the following detailed description. It should be understood, however, that various changes and modifications within the spirit and scope of the invention will become apparent to those skilled in the art from this detailed description.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6a depicts a front view of a third embodiment;

FIG. 6b illustrates the-use of the second alternate embodiment of FIG. 6a;

FIG. 6c shows a cross-section of the right side view of the second embodiment in FIG. 6a;

FIG. 6d shows a top view of the second embodiment in FIG. 6a; and

DESCRIPTION OF THE PREFERRED EMBODIMENTS

Figure 1:
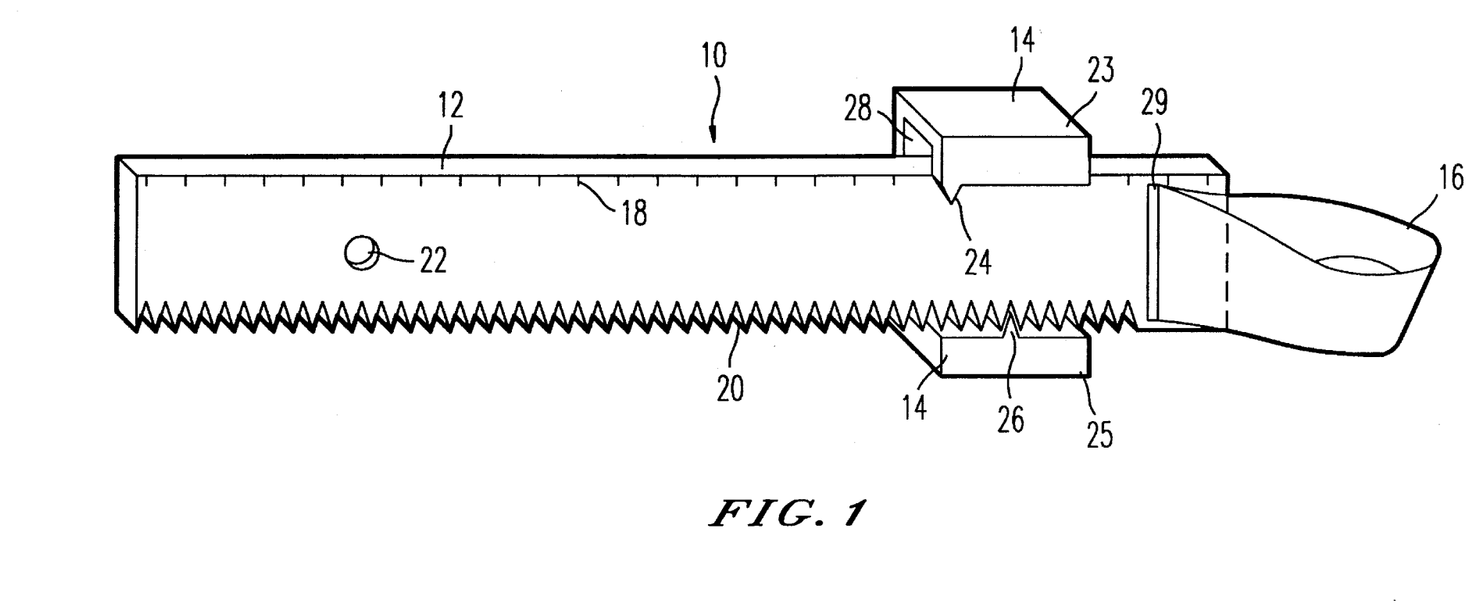
FIG. 1 is a perspective view of the locking orthodontic band gauge.

Referring now to the drawings, wherein like reference numerals designate identical or corresponding parts throughout the several views, and more particularly to FIG. 1 thereof, a locking orthodontic band gauge is shown that more accurately measures an orthodontic band size.

FIG. 1 shows the locking orthodontic band gauge 10 and its general dimensions. The gauge 10 should be elongated such that the gauge may be inserted deep into a patient's mouth. Although this figure depicts the gauge 10 as rectangular, any shape may be employed so long as the gauge 10 is sufficiently thin, allowing an operator to easily manipulate the gauge 10 within the limited space of a patient's mouth. In addition the gauge 10 should be manufactured using materials that are easily sterilized, such as plastic and stainless steel.

The gauge 10 of FIG. 1 comprises an elongated main portion or probe 12, a locking indicator assembly 14 and a gauge loop 16. The probe 12 is placed in a patient's mouth and the loop 16 is secured around a tooth. The loop 16 is fixed to the locking indicator assembly 14 so that as the assembly is moved along the probe 12, the loop 16 tightens about the tooth.

The probe 12 includes a scale 18 on one side and teeth-like locking portions at discrete positions 20 on the opposite side. The scale indicates the band size and the teeth lock the indicator in place.

The locking indicator assembly 14 functions as a positive lock, is slidable mounted on the probe 12, and is kept from sliding off the gauge 10 by screw stop 22. The locking indicator assembly 14 includes a depressible head 23 having an indicator needle 24, positioned adjacent to the scale 18, to indicate an orthodontic band size. The locking indicator assembly 14 further includes a locking tooth head 25 connected to the depressible head 23 and having a locking tooth 26 that engages any of the teeth 20 along the probe 12 thereby positively locking the assembly 14 in place at discrete positions. The locking indicator assembly 14 is unlocked by depressing the depressible head 23 into the depressible head recess area 28 causing the connected locking tooth head 25 to move away from the probe 12 and disengage the locking tooth 26 from the teeth 20. The unlocking indicator assembly 14 then may be repositioned to other points along the probe 12.

The gauge loop 16 extends from the loop dispenser 29 and is connected to the locking indicator assembly 14. As the indicator assembly 14 advances toward the screw stop 22, the loop 16 is pulled into the dispenser 29 and the loop circumference is decreased. Conversely, as the indicator assembly advances toward the loop 16, the loop 16 is dispensed from the dispenser 29 and its circumference is increased.

Figure 2A:
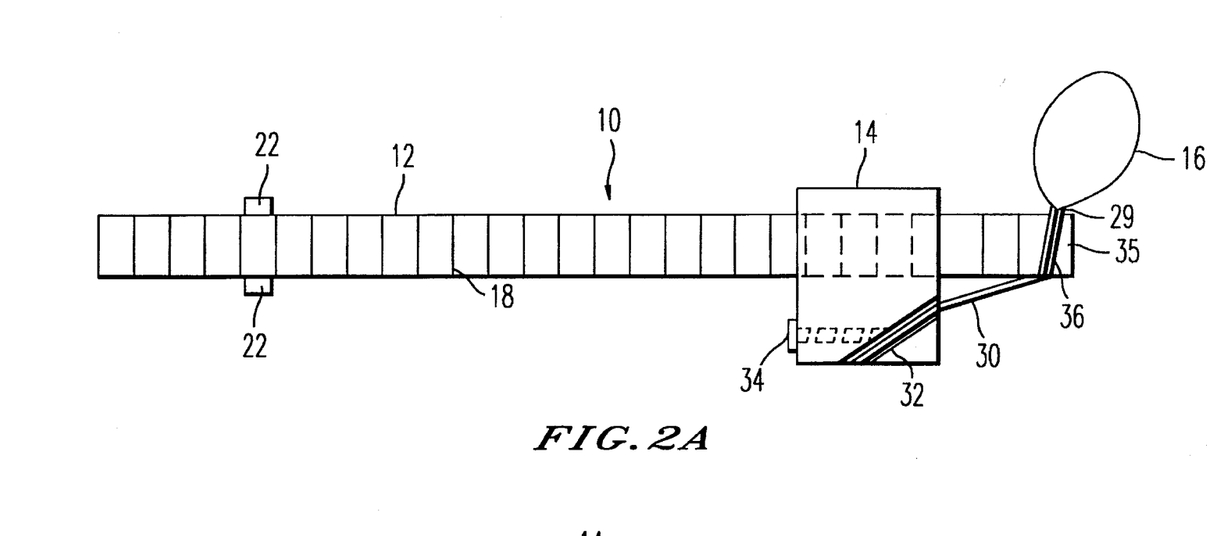
FIG. 2a depicts a bottom view of the locking orthodontic band gauge of FIG. 1.
Figure 2B:
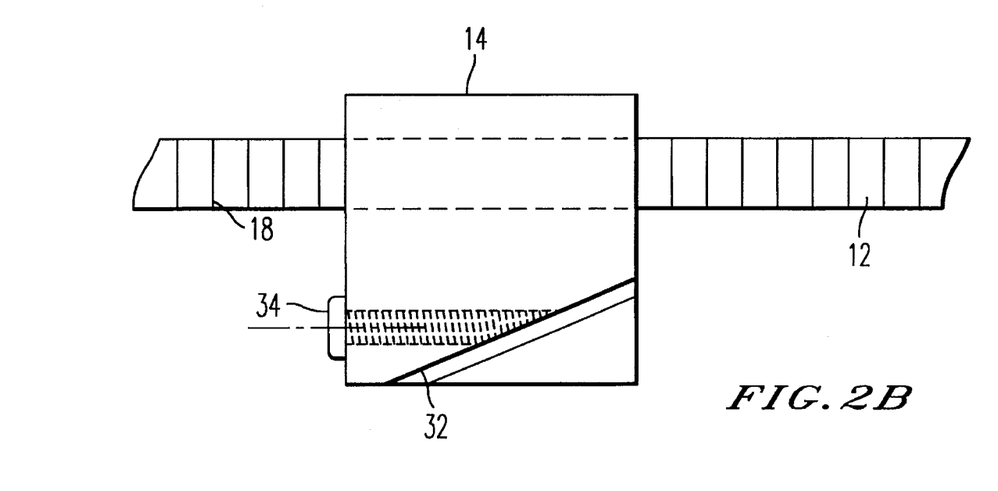
FIG. 2b is a magnified view of a locking indicator assembly as shown in FIG. 2a mounted on the orthodontic band gauge.

FIGS. 2a and 2b demonstrate how the gauge loop 16 is connected to the locking indicator assembly 14. Loop 16 comprises gauge tape 30 that is fitted into locking indicator assembly 14 by threading the tape 30 into the indicator tape slot 32. The tape 30 is held within the indicator tape slot 32 by a holding screw 34. The tape 30 exits the indicator assembly 14, travels along the probe 12, and feeds into the probe head 35 through the probe tape slot 36 of the probe 12. The tape 30 exits the probe 12 from the dispenser 29 and forms loop 16.

When an operator unlocks the indicator assembly 14 and advances the assembly 14 away from the probe head 35, the tape 30 is pulled through the probe tape slot 36. This causes a portion of the loop to enter the dispenser 29, where the loop is pinched off, thereby decreasing the circumference of the loop 16.

Indicator tape slot 32 and probe tape slot 36 have an opening on one side of the band gauge 10 to allow an operator to easily thread the tape 30. These openings may be on alternate sides of the band gauge 10 so that the tape 30 does not easily slip out.

The holding screw 34 holds the tape 30 within the locking indicator assembly 14. Further, the screw 34 may be loosened to allow an operator to adjust the length of the tape 30 within the indicator tape slot 32 or thread an entirely new lengthened tape into the band gauge 10. By changing the length between the indicator assembly 14 and the loop 16, an operator is able to set the indicator assembly at any point along the probe 12. In this manner, an operator may adjust the indicator assembly 14 to a point where the orthodontic band gauge 10 is comfortable when held. In addition indicator assembly 14 may be positioned substantially outside a patient's mouth to allow an operator to easily read a band size from the orthodontic band gauge 10.

Further, the indicator tape slot 32 and probe head tape slot 36 openings, allowing an operator to easily replace the tape 30, also provide easy sterilization of the tape 30 and loop 16. An orthodontist simply removes an already used tape 30 and replaces it with a sterilized one.

The tape 30 should be made out of a material that is flexible yet sufficiently rigid since the tape 30 is forced through the probe tape slot 36 by a translational force from the indicator assembly 14, advanced toward the probe head 35 by an operator. The loop 16 should also be flexible yet sufficiently rigid so that the loop 16 can close about an irregularly shaped tooth, fit between tightly spaced teeth, and be removed while enclosed about a tooth.

To further encourage the guiding of the tape 30 through the probe tape slot 36, the indicator tape slot 32 and probe tape slot 36 should be angled such that the tape 30 enters the probe tape slot 36 at an obtuse angle, not a radical acute angle. In this fashion, the tape 30 will not pucker when passing from the indicator tape slot 32 through the probe tape slot 36.

Figure 3:
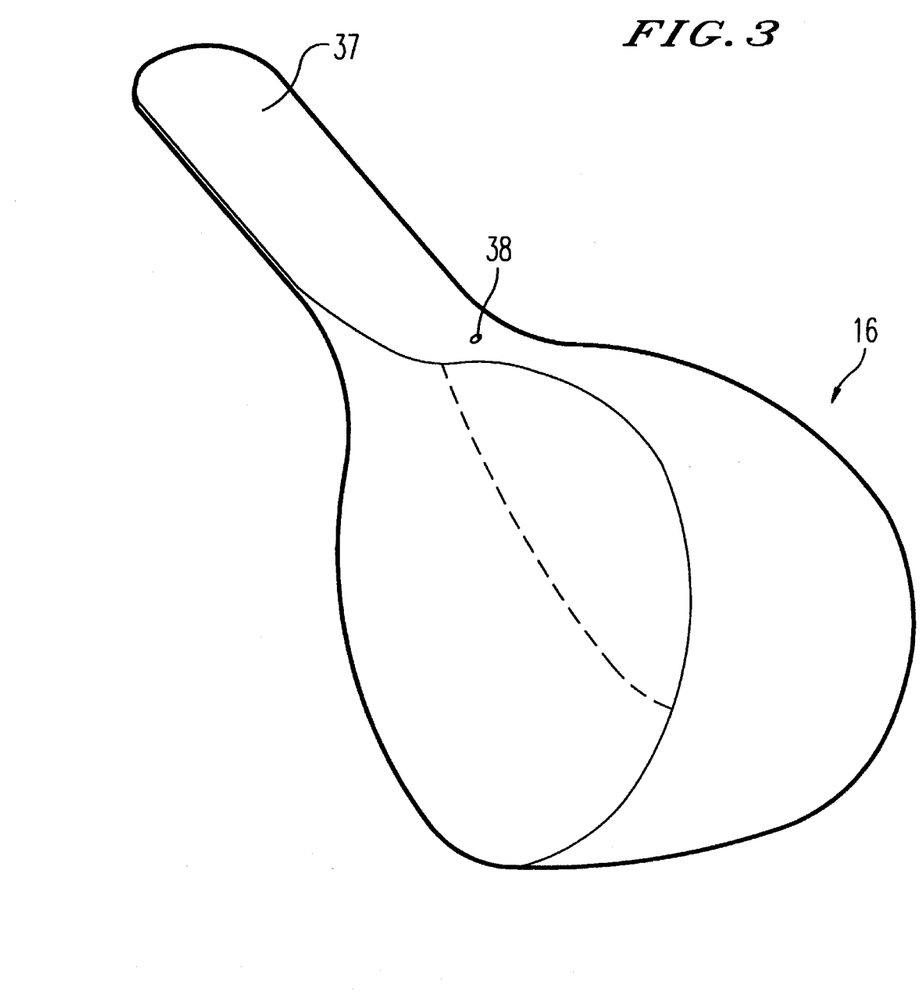
FIG. 3 is an enlarged perspective view of the orthodontic band gauge loop.

FIG. 3 is a perspective view of the gauge loop 16 that is placed around a tooth for measurement of an orthodontic band size.

In the preferred embodiment, the loop is not fixed at one end of the orthodontic band gauge 10. Instead, the loop is welded at a weld point 37, chosen at a point that is sufficient to allow the loop 16 to fit around any human tooth size.

The orthodontic band gauge 10 is superior to circular micrometers, typically having one end of a loop fixed to the micrometer, because the band gauge 10 pulls on both sides of the loop 16 evenly when placed around a tooth and tightened. By welding the gauge loop 16 at a weld point 37 each side of the loop 16 is pulled with equal force when pulled through the probe head 35. Should the loop 16 be fitted around a tooth between tightly spaced teeth, pinching the loop 16, the band gauge 10 will still be able to indicate an accurate band size because the loop 16 is tightened from both sides where the loop 16 is pinched. In a circular micrometer having one end fixed to the micrometer, only one side is pulled, leaving the other side untightened beyond a pinch.

In practice, orthodontic bands are not customarily manufactured in sizes greater than a 45 millimeter circumference. Therefore, the weld point 37 is chosen at a point to allow the loop 16 to easily fit around a 45 millimeter circumference tooth. In addition, a 45 millimeter marking 38 is made on the circumference of the loop 16 to allow an operator to quickly determine the approximate size of the loop 16.

The 45 millimeter marking 38 also allows an operator to calibrate the orthodontic band gauge 10. As discussed, the locking indicator assembly 14 may be set at different points along the probe 12 using different lengthened gauge bands 30. To calibrate the band gauge 10, an operator may simply set the indicator 14 to the desired position, pulling the tape 30 through the probe tape slot 36 until the 45 millimeter marking 38 is flush with the dispenser 29, and tightening the holding screw 34. When the gauge 10 is calibrated, the indicator needle 24 will point to a point on the scale corresponding to a gauge loop 16 with a circumference of 45 millimeters. Taking note of the position of the scale the indicator 14 may be advanced away from the probe head 35, enclosing the loop 16 about a tooth. The difference between the calibrated position and an enclosed position is then subtracted from the calibrated position, indicating the correct orthodontic band size.

Figures 4A, 4B:
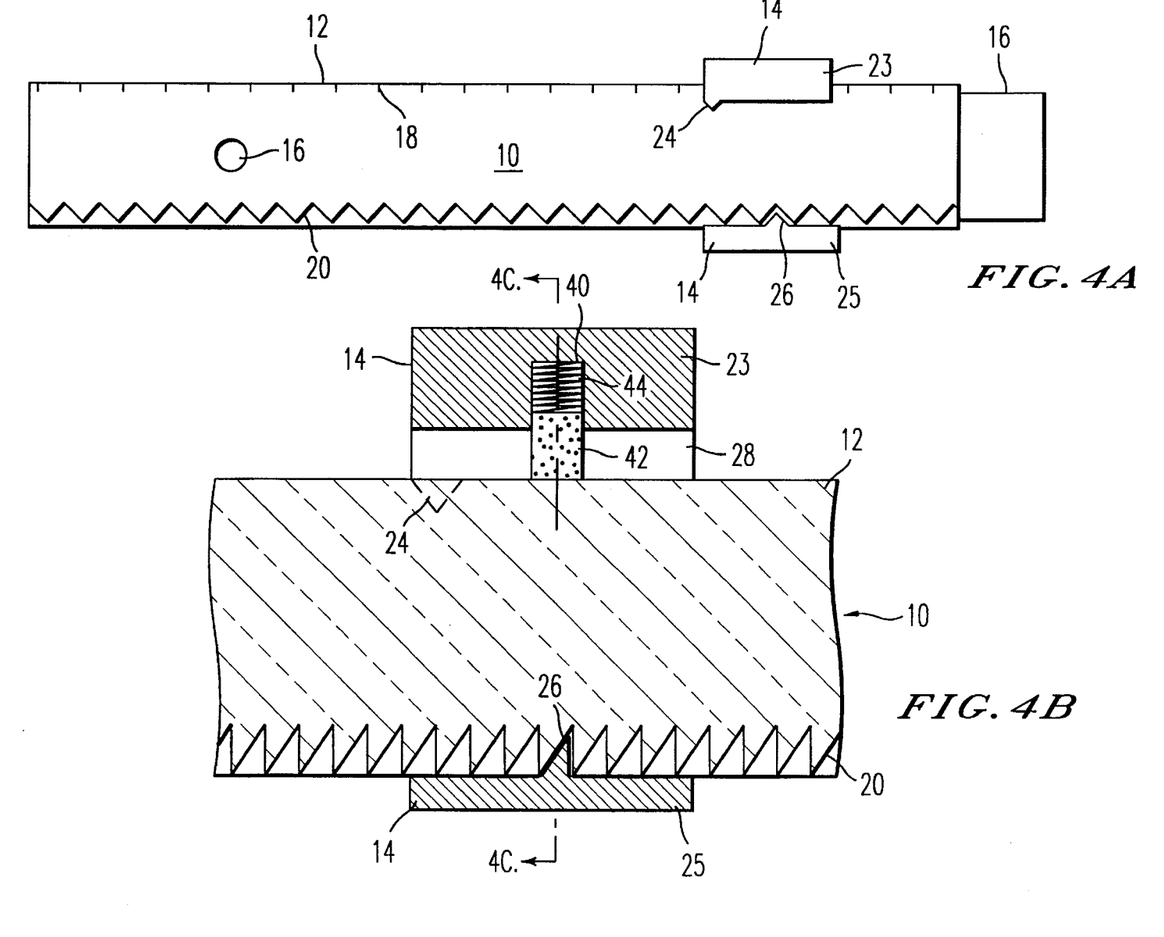
FIG. 4a depicts the front view of the locking orthodontic band gauge of FIG. 1.
FIG. 4b is an enlarged vertical cross-sectional view of the locking indicator assembly taken substantially on the line 4b—4b of FIG. 4c.

FIG. 4a shows the locking orthodontic band gauge 10 with the locking tooth 26 of the locking tooth head 25 engaging the teeth 20. The indicator needle 24 of the depressible head 23 is shown pointing to one of the scales 18.

To reposition the locking indicator assembly, the depressible head 23 is depressed toward the probe 12 causing the connected locking tooth head 25 and locking tooth 26 to translationally disengage the teeth 28. Once disengaged, an operator may reposition the indicator assembly 14 at any point along the probe 12.

The spacing between the teeth is proportional to the increment at which the loop 16 circumference changes. The larger the teeth 20, the greater the increment between each loop circumference. Therefore, the teeth 20 of the probe 12 may be constructed significantly fine to allow the band gauge 10 to tighten about teeth in finer increments, providing a more accurate measurement.

The finite increments of the teeth do not substantially decrease the accuracy of the orthodontic band size measurement. The exact measurement of a tooth in millimeters is not required because orthodontic bands are not manufactured with every millimeter circumference, but in standard sizes. Therefore, measuring a tooth in millimeters does not aid in determining a standard orthodontic band size, but only provides an orthodontist with an approximation.

The preferred embodiment employs teeth that are spaced at intervals corresponding to standard orthodontic band sizes. Therefore, an orthodontic band size is indicated by the present invention, not a millimeter circumference, taking the guess work out of choosing orthodontic band sizes.

FIG. 4b shows a magnified cross-section of the locking indicator assembly 14 engaging the teeth 20 as shown in FIG. 4a. The depressible head 23 is kept tensionally distant from the probe by spring 40 and dowel 42. The spring 40 is positioned in dowel recess 44 having one end in contact with the depressible head 23. A dowel 42, with a portion extending into the dowel recess 44, is positioned in contact between the other end of the spring 40 and the probe 12. The dowel 42 and spring 40 causes the depressible head 123 to resist entering the depressible head recess 28. The locking tooth head 25 and locking tooth 26 are connected to the depressible head and are caused to engage the teeth 20 through translational tension of the dowel 42 and spring 40. This engagement causes the locking indicator assembly 14 to be locked into position and prevents the depressible head 23 from springing off the probe 12.

The dowel recess 44 is shown to be slightly longer than the length of the locking tooth 26 to ensure that the locking tooth 26 will completely disengage the teeth 20 when the depressible head 23 is depressed.

Figure 4C:
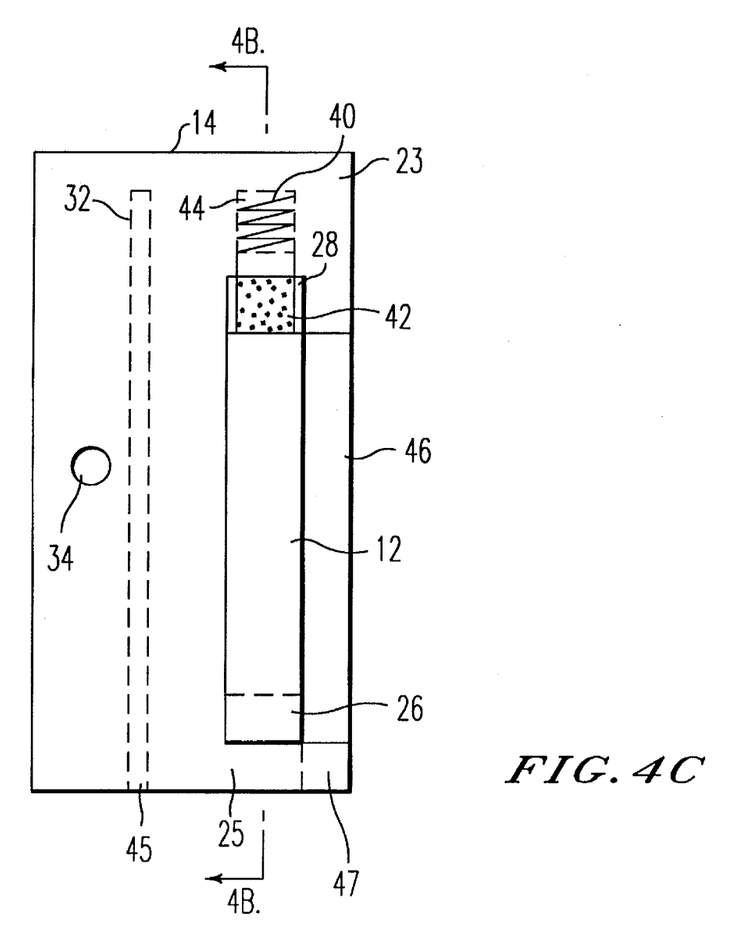
FIG. 4c is a vertical cross-sectional view of the locking indicator assembly mounted taken substantially on the line 4c—4c of FIG. 4b.

FIG. 4c is a cross-sectional view from the right side of the orthodontic band gauge as shown in FIGS. 4a and 4c, showing the components comprising the locking indicator assembly 14. The indicator tape slot 32 is shown having an opening 45 on one side of the indicator assembly 14 for easily threading the gauge tape 30. The holding screw 34 is shown adjacent the tape slot 32. The depressible head 23 and locking tooth head 25 with locking tooth 26 are clearly shown connected and enclosed about the probe 12.

For further securing the indicator assembly 14 to the probe 12, the indicator assembly 14 may also include a crossbar 46 that extends from the depressible head 23 across the probe 12 and through a crossbar opening 47 in the locking tooth head 25.

Figure 5:
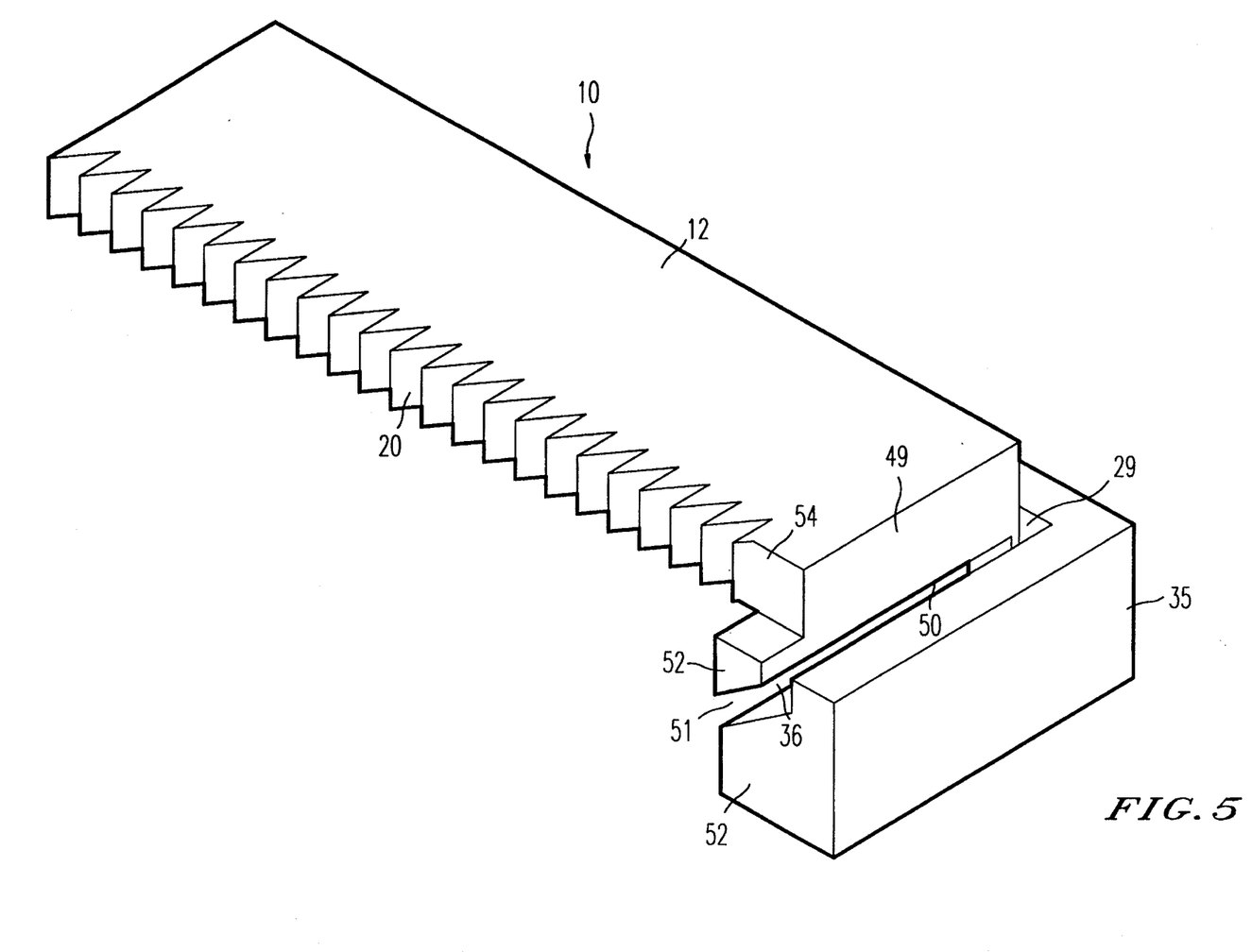
FIG. 5 is a perspective view of a second embodiment of the locking orthodontic band gauge.

FIG. 5 is a perspective view of a second embodiment including a probe head platform 49. The platform 49 is positioned at one end of the probe 12 in close proximity with the probe head 35 such that a space is left therebetween forming the probe tape slot 36.

The platform 49 includes a band access area 50 that allows a gauge tape 30 to enter the probe head slot 36 closer to the dispenser 29. This arrangement allows the tape 30 to enter the probe tape slot 36 at an even greater obtuse angle than in the previous embodiment, providing a smoother path for the tape 30 to travel. In addition, the band access area is angled in the direction toward the dispenser to further facilitate a smooth path for the tape 30. The band access area 50 further includes an opening 51 on one side of the band gauge 10 allowing ease of threading the tape 30.

The platform 49 also includes stops 52 for stopping the locking tooth head 25 from advancing past the probe head 35. A locking tooth head recess 54 is incorporated into the platform 49 to receive a portion of the locking tooth head 25, allowing the tooth head 25 to advance as far as possible until the locking tooth 26 meets the stops 52.

FIGS. 6a, 6b, 6c and 6d show a third embodiment providing a locking orthodontic band gauge 10 that is easy to operate using one hand and provides excellent leverage on the gauge loop 16.

Figures 6A, 6C, 6D:
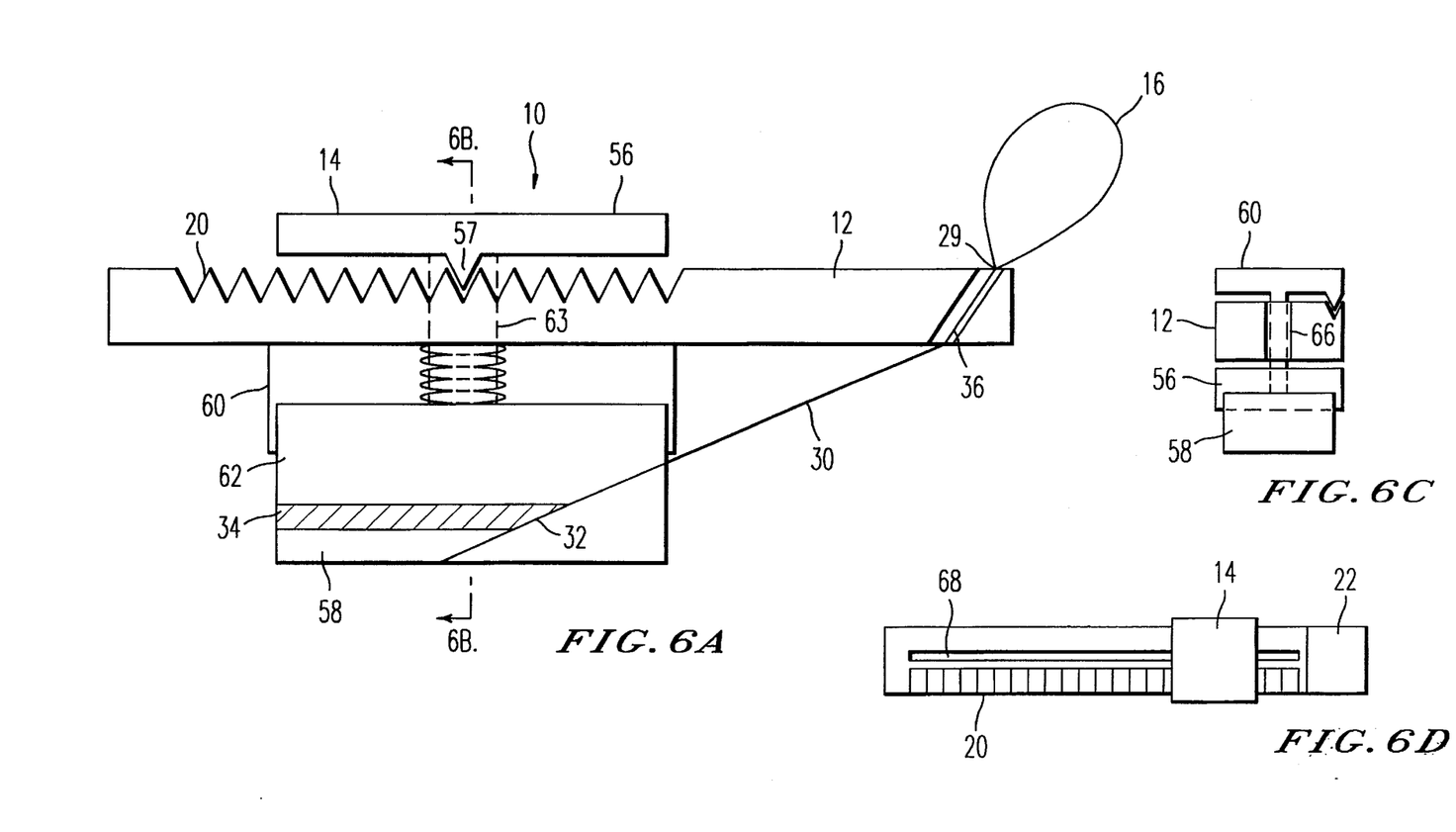

FIG. 6a shows a front view of the third embodiment, clearly showing the locking tooth head 56, depressible head 58 and the gauge loop 30 all in parallel planes. Similar to the embodiment of FIG. 1, a locking indicator assembly 14 comprises a locking tooth head 56 with a locking tooth 57 connected to a depressible head 58. The indicator assembly 14 is unlocked and repositioned along the probe 12. A holding screw 34 is also provided for purposes of calibration and sterilization. In this embodiment, the depressible head 58 is mounted in a spring mounting cover 60 including a spring 62 for tensionally forcing the depressible head 58 away from the probe 12. The depressible head 58 is connected to the tooth locking head 56 by an indicator arm 63 causing the locking tooth 57 to tensionally engage the teeth 20 and locking the indicator assembly 14.

Figure 6B:
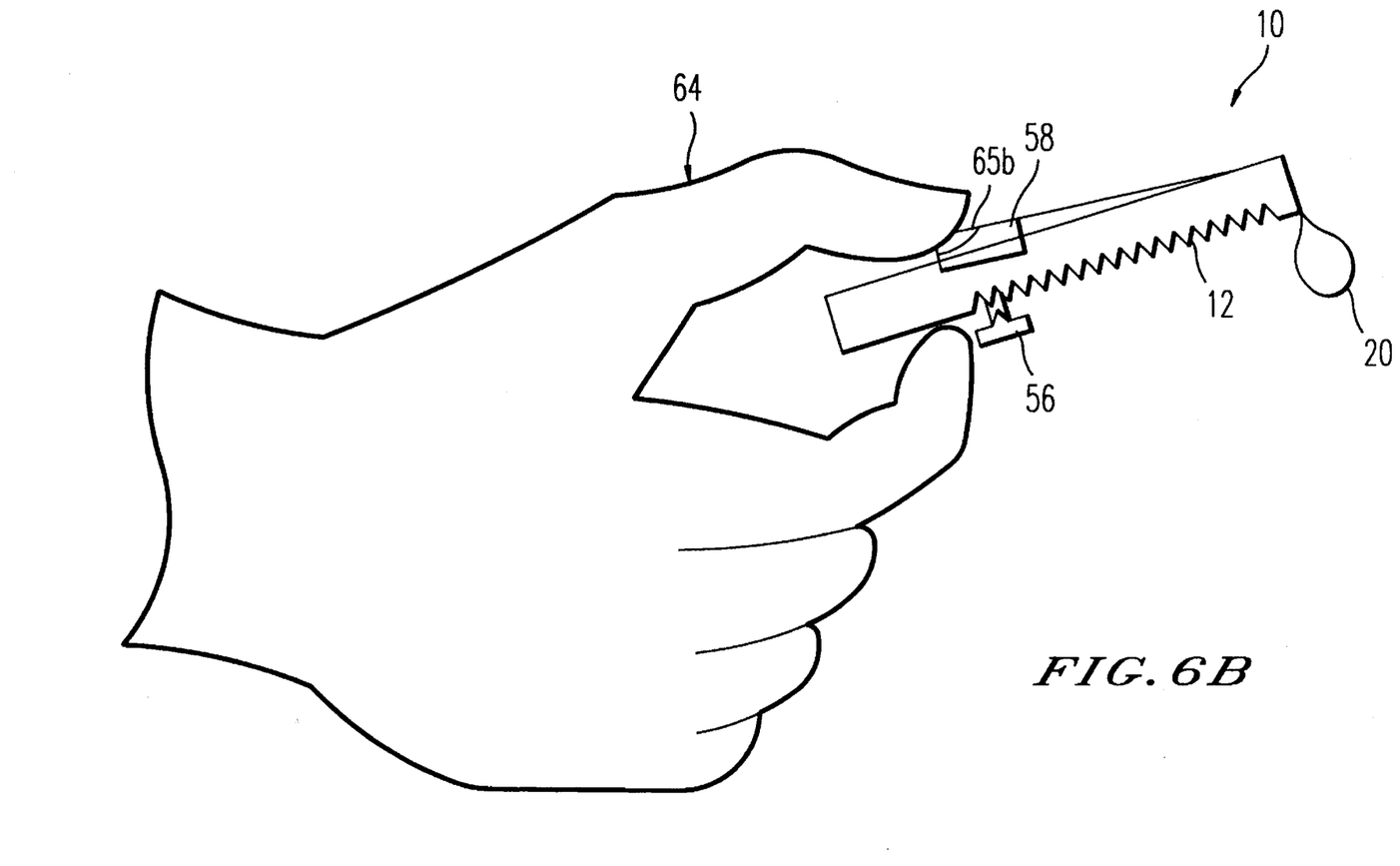

This arrangement allows an operator to easily operate the gauge 10 with one hand grasping the probe by "pinching" the gauge 10 as shown in FIG. 6b. An operator's hand 64 holds the probe 12 between thumb and forefinger. With the same hand 64, the thumb is able to depress, unlock and reposition the indicator assembly 14 along the probe 12. This natural hand position allows an operator to apply excellent leverage on the band loop 20 using only one hand 64. Since two hands are not required to operate the gauge 10 of FIG. 6a, an operator is able to see more clearly into a patient's mouth, facilitating a correct band size measurement.

A thumb groove 65b may be provided allowing an operator to grip the probe 12 more easily and force the indicator assembly 14 with even greater leverage.

FIG. 6c shows a cross-section view from the right side of the gauge 10 in FIG. 6a. FIG. 6d is a top view of the gauge 10 in FIG. 6a. These figures show an arm slot 66 that receives the indicator arm 63 and allows the locking indicator assembly 14 to slide along the probe 12. The arm slot 66 is positioned within the body of the probe 12 to provide extra stability of the indicator 14 mounted to the gauge 10.

Figure 7:
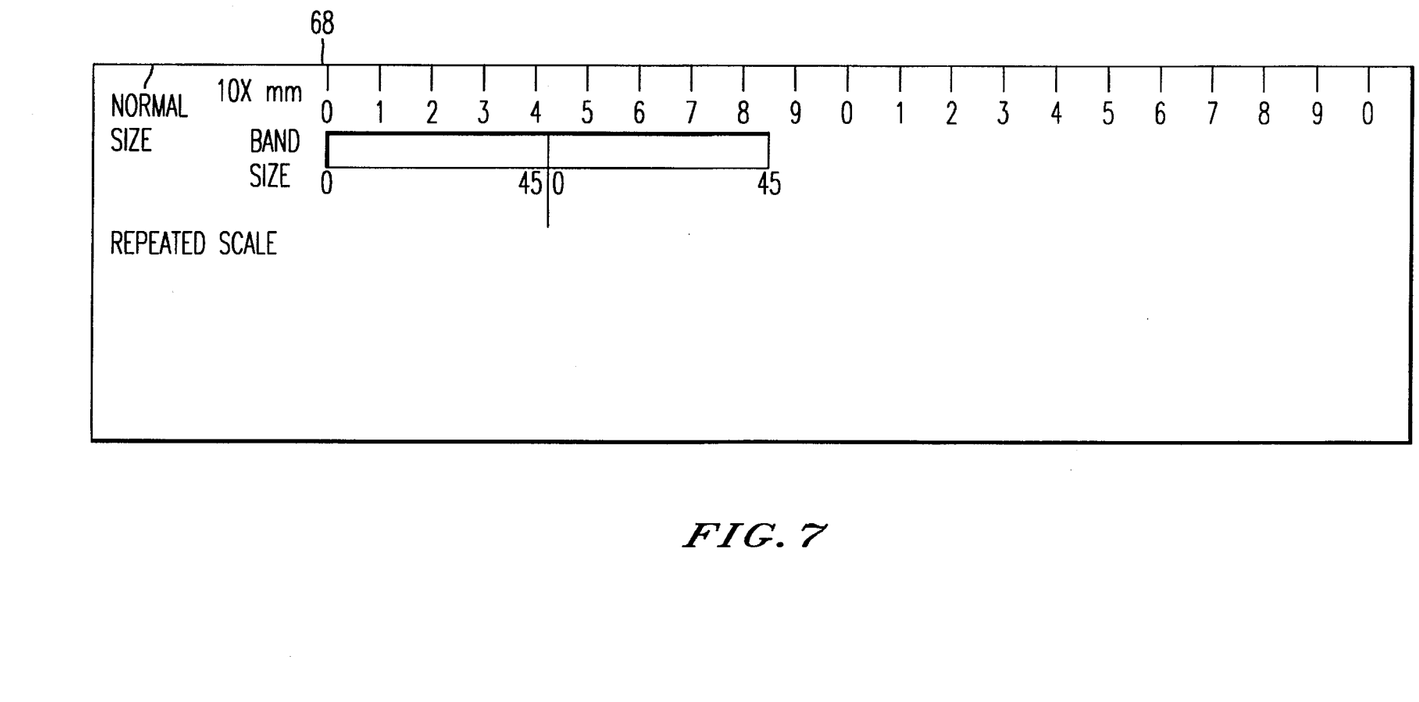
FIG. 7 depicts a fourth embodiment of the locking orthodontic band gauge including different sets of scales.

FIG. 7 shows a fourth embodiment of the gauge wherein different sets of scales are provided on the probe 12.

Normal scale 68 is a conventional millimeter scale. This normal scale may be used when calibrating the orthodontic band gauge 10 using the 45 millimeter marking 38. As discussed, the gauge 10 is calibrated by positioning the marking 38 flush with the dispenser 29 and noting the position of the indicator needle 24. The loop 16 is enclosed about a tooth and the difference between the calibrated position and the enclosed position is subtracted from the 45 millimeter position, indicating the correct orthodontic band size.

The band size scale 70 is also provided listing standard band sizes. The band sizes are displayed in repeated sets from a smallest size to a largest size (45 mm) with the largest size of each set nearest the probe head 35.

An operator sets the locking indicator assembly 14 at any convenient position starting at the largest band size on any of the repeated band sizes. The gauge loop 16 is calibrated, with the 45 millimeter marking 48 flush with the dispenser and placed around a patient's tooth. The indicator assembly 14 is advanced away from the probe head 35 to enclose the loop 16 about the tooth. As the indicator assembly 14 is moved away from the probe head 35, the indicator needle 24 will advance along the corresponding band size set. When the loop 16 is fully enclosed about a tooth the indicator needle 24 will indicate the correct band size.

A repeated millimeter scale 72 is also provided on the probe 12 that indicates repeated sets of 45 millimeter long scales with the 45 millimeter markings of each set nearest the probe head 35. Similar to calibrating the band gauge 10 for the band size scale 70, an operator positions the indicator assembly 14 at any of the 45 millimeter scales along the repeated millimeter scale 72 and adjusting the gauge tape 30 within the depressible head slot so that the 45 millimeter marking 38 on the gauge loop 16 is flush with the dispenser. The loop 16 is enclosed about a tooth and a millimeter marking is indicated by the indicator needle 24. Both the band size scale 70 and repeated millimeter scale 72 may be displayed on the probe 12 adjacent to each other such that the band size and millimeter circumference of the tooth are indicated simultaneously.

In summary, a locking orthodontic band gauge 10 is provided that more accurately determines an orthodontic band size, thereby reducing the risk of oral infections, discomfort and cost. A locking indicator assembly 14 locks the loop 16 in place so that the band size measured is not disturbed during a fitting procedure. The calibration of the indicator assembly 14 allows an orthodontist to operate the gauge comfortably and provides for reading the indicator outside of a patient's mouth. Further, the loop 16 is pulled through the dispenser 29, evenly on both sides, allowing the gauge 10 to firmly tighten around a tooth. In the third embodiment, a locking orthodontic band gauge 10 is provided with all of the components in the same plane, providing better handling and tightening capabilities. Finally, a fourth embodiment provides different sets of scales so that an operator can easily determine the band size of an orthodontic band without approximating.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A locking orthodontic band gauge for determining an orthodontic band size, comprising:
   an elongated main portion;
   a locking indicator assembly slidably mounted on the main portion;
   a loop cooperatively associated with the main portion and the locking indicator assembly such that when the indicator assembly is slid along the main portion, the size of the loop circumference is changed; and
   a series of locking portions spaced along the length of the elongated main portion at discrete positions and cooperating with said locking indicator assembly to selectively lock the indicator assembly at the discrete positions.

2. A locking orthodontic band gauge in accordance with claim 1, wherein the locking indicator assembly further comprises:
   a locking tooth head including a locking tooth that mates with the locking portions at discrete points.

3. A locking orthodontic band gauge in accordance with claim 2, wherein the locking indicator assembly further comprises:
   a biasing mechanism biasing the locking tooth into engagement with one of the locking portions.

4. A locking orthodontic band gauge in accordance with claim 3 wherein the biasing mechanism comprises:
   a depressible head forming one part of the indicator assembly, opposite the locking tooth head, and adjacent to the main portion, forming a depressible head recess therebetween; and
   a tension mechanism biasing the depressible head away from the main portion such that the depressible head enters the head recess when a sufficient force acts thereon.

5. A locking orthodontic band gauge according to claim 4 wherein the tension mechanism comprises:
   a dowel recess within the depressible head;
   a spring positioned within the dowel recess; and
   a dowel having one end in engagement with the spring and the other end in engagement with the main portion.

6. A locking orthodontic band gauge in accordance with claim 1 further comprising:
   a scale on the main portion; and
   an indicator needle associated with the locking indicator assembly and cooperating with the scale to indicate an orthodontic band size.

7. A locking orthodontic band gauge in accordance with claim 1, wherein the loop comprises a tape having ends fixed to the indicator assembly, the tape extending through a slot in the elongated main portion and emerging from the slot on a side of the main portion opposite the side where the tape is fixed to the indicator assembly to form the loop.

8. A locking orthodontic band gauge in accordance with claim 7, wherein the tape further comprises:
   a welding point locking the ends of the tape to one another such that the ends of the tape are acted upon by the locking indicator assembly with equal force.

9. A locking orthodontic band gauge in accordance with claim 8, wherein the tape further comprises:

a 45 mm marking for indicating when the locking indicator is slid along the main portion and the loop has a circumference of 45 mm.

10. A locking orthodontic band gauge in accordance with claim 1, wherein the main portion further comprises:

a probe head holding the loop at one end of the main portion; and a band access area positioned within the probe head and receiving the loop at an obtuse angle with the locking indicator assembly and providing a smooth transition between the locking indicator assembly and the probe head.

11. A locking orthodontic band gauge in accordance with claim 1 further comprising:

a depressible head forming a part of the locking indicator assembly and having a recess between the head and the main portion;

a locking tooth head connected to the depressible head and having a locking tooth engaging the locking portions so that the locking indicator assembly is locked in a position along the main portion, the locking tooth head being positioned in a parallel plane; gauge tape connecting the locking indicator assembly to the loop;

an indicator tape slot holding the gauge tape within the locking indicator assembly, the slot having an opening that is in a parallel plane with the depressible head and locking tooth head wherein the tape is threaded within the slot;

a scale in a plane parallel to the plane of the locking tooth head; and an indicator needle connected to the depressible head so that an operator may slide the assembly using one hand and reading the orthodontic band size from the indicator needle.

12. A locking orthodontic band gauge in accordance with claim 11 wherein the depressible head further comprises:

a depressible head recess;

a spring positioned within the depressible head recess; and a dowel with one end extending into the dowel recess engaging the spring and the other end engaging the probe means, the spring and dowel tensionally forcing the depressible head away from the main portion.

13. A locking orthodontic band gauge in accordance with claim 1, wherein the main portion further comprises:

a normal scale having units displayed in millimeters;

a band size scale repeated along the main portion; and a repeated millimeter scale adjacent to the band size scale and repeated in sets of 45 mm so that an operator may calibrate the locking orthodontic band gauge at different points along the main portion.

14. A locking orthodontic band gauge according to claim 13 wherein the normal scale, band size scale and repeated millimeter scale are displayed such that they correspond to the discrete positions of the locking portions.

15. A locking orthodontic band gauge to be fitted around a patient's tooth for determining an orthodontic band size, comprising:

a probe supporting a gauge tape such that the gauge tape can be fitted around the tooth by insertion of the probe into the patient's mouth, the probe being sufficiently long so as to be inserted within the patient's mouth;

an indicator associated with the probe and movable relative to the probe, said indicator indicating the orthodontic band size of the patient's tooth when the gauge tape is fitted around the tooth; and a spring biased lock positively locking the indicator relative to said probe such that the indicator is maintained stationary during an orthodontic band size fitting wherein said lock has a depressible head which is spring biased, said head being depressible and permitting movement of the lock along the probe in determining the orthodontic band size of the patient's tooth.

16. A locking orthodontic band gauge in accordance with claim 15, wherein the probe comprises:

an elongated probe sufficiently thin to fit within a patient's mouth, allowing an operator to easily manipulate the gauge tape.

17. A locking orthodontic band gauge in accordance with claim 15, wherein the gauge tape comprises a loop and wherein the indicator comprises:

a locking indicator assembly associated with the loop and slidably mounted along the probe so that when the assembly is slid, the circumference of the loop changes size; and a scale located along the probe and adjacent to the locking indicator assembly, said scale indicating the orthodontic band size when the loop is tightly positioned about the tooth.

18. A locking orthodontic band gauge to be fitted around a patient's tooth for determining an orthodontic band size, comprising:

a probe supporting a gauge tape such that the gauge tape can be fitted around the tooth by insertion of the probe into the patient's mouth, the probe being sufficiently long so as to be inserted within the patient's mouth;

an indicator associated with the probe and movable relative to the probe, said indicator indicating the orthodontic band size of a patient's tooth when the gauge tape is fitted around the tooth;

a lock positively locking the indicator relative to the probe such that the indicator is maintained stationary during an orthodontic band size fitting, wherein the lock comprises:

a plurality of protrusions positioned along discrete points on the probe;

a depressible head forming a part of the locking indicator assembly and having a recess between the depressible head and the probe; and a locking tooth head connected to the depressible head and having a locking tooth engaging the protrusions along the probe so that the locking indicator assembly is locked into position and unlocked when the depressible head is depressed into the recess.

19. A locking orthodontic band gauge according to claim 18, wherein the lock comprises:

a tensioner associated with the depressible head, said tensioner maintaining tension on the depressible head and causing the depressible head to resist being depressed into the recess, such that the locking tooth head disengages the probe when a sufficient force is applied to the tensioner.

20. A locking orthodontic band gauge according to claim 19, wherein the tensioner comprises:

a dowel recess within the depressible head;

a spring positioned in the dowel recess; and a dowel with one end extending into the dowel recess engaging the spring and the other end engaging the probe, the spring and dowel tensionally forcing the depressible head away from the probe.

* * * * *